(12) United States Patent
Park (10) Patent No.: US 11,484,906 B2
(45) Date of Patent: Nov. 1, 2022

(54) HANDPIECE OF SKIN CARE DEVICE (71) Applicant: DAONIC CO., LTD., Seoul (KR)

(72) Inventor: Chang Guk Park, Uijeongbu-si (KR)

(73) Assignee: DAONIC CO., LTD., Seoul (KR)

( * ) Notice: Subject to any disclaimer, the term of this patent is extended or adjusted under 35 U.S.C. 154(b) by 1109 days.

(21) Appl. No.: 15/999,641

(22) PCT Filed: Feb. 20, 2017

(86) PCT No.: PCT/KR2017/001836
§ 371 (c)(1),
(2) Date: Sep. 14, 2018

(87) PCT Pub. No.: WO2017/142379
PCT Pub. Date: Aug. 24, 2017

(65) Prior Publication Data
US 2020/0338586 A1 Oct. 29, 2020

(30) Foreign Application Priority Data

Feb. 18, 2016 (KR) .................. 10-2016-0019039

(51) Int. Cl.
*B05C 17/005* (2006.01)
*B08B 3/02* (2006.01)
*B08B 5/04* (2006.01)

(52) U.S. Cl.
CPC ........ *B05C 17/00503* (2013.01); *B08B 3/026* (2013.01); *B08B 5/04* (2013.01); *B08B 2203/0229* (2013.01)

(58) Field of Classification Search
None
See application file for complete search history.

(56) References Cited

FOREIGN PATENT DOCUMENTS

| KR | 20-0412689 | 3/2006 |
| KR | 20-0427899 Y1 | 10/2006 |
| KR | 10-0946363 | 3/2010 |
| KR | 10-1437563 | 7/2014 |
| KR | 10-1483559 B1 | 1/2015 |
| KR | 10-1505813 B1 | 3/2015 |
| KR | 10-2015-0060208 A | 6/2015 |
| KR | 10-2015-0137527 A | 12/2015 |

OTHER PUBLICATIONS

Google Patents translation of KR101483559B1 retrieved from https://patents.google.com/patent/KR101483559B1/en?oq=101483559 on Mar. 2, 2022 (Year: 2022).*

* cited by examiner

*Primary Examiner* — Eric W Golightly
(74) *Attorney, Agent, or Firm* — Maschoff Brennan (57) ABSTRACT

A handpiece of a skin care device is disclosed. The handpiece includes a body part having an attaching and detaching hole provided on one side thereof, a solution introducing part linked with the attaching and detaching hole, an air discharging part, and a disposable tip module mounted onto the attaching and detaching hole of the body part. The tip module includes a cylinder body detachably mounted onto the attaching and detaching hole, and an inner cylinder configured to have a hollow inside and installed in the cylinder body. The hollow inside of the inner cylinder is linked with the solution introducing part and is configured as a solution injection flow channel in which a solution introduced from the solution introducing part flows when the tip module is mounted onto the attaching and detaching hole.

5 Claims, 7 Drawing Sheets

HANDPIECE OF SKIN CARE DEVICE

TECHNICAL FIELD

The present invention relates to a handpiece of a skin care device and more specifically, to a handpiece used for a skin care device which is capable of injecting medicine for cleaning and improving skin etc. by spraying a solution for skin care and injecting the same into skin.

DESCRIPTION OF THE RELATED ART

In recent years, there has been a growing interest in skin care among men and women regardless of their ages. Against this backdrop, various devices for skin care have been developed, and dermatology clinics and skin care centers have sprung up like mushroom after rain.

These days, the procedure of microneedling combined with conventional fractional laser technology is well-known. In the procedure, micro needles are inserted into skin so as to set up pillars for treatment and deliver radio frequency to the skin. Accordingly, thermal damage is done to a local area in the skin, and tiny puncture wounds are made in the skin so as to facilitate regeneration of the skin ranging from epithelium to corium and to induce growth factors to stimulate the healing and rejuvenation of the skin.

In general, when radio frequency is applied to human tissue through microneedles serving as electrodes for supplying radio frequency, frictional heat is generated inside the tissue around the microneedles so as to promote the regeneration of collagen in corium. As a result, wrinkles are reduced and pores are tightened.

In the above-described procedure, high-temperature thermal energy is delivered to a target area of skin so as to facilitate the regeneration of collagen and elastin fibers thereby treating acne, acne scars, fine line and wrinkles, and large pores without causing burns in epidermis. Additionally, the procedure helps to increase blood flow, facilitate fat burning, and improve the lymphatic circulation thereby making it possible to treat obesity.

South Korean Patent No. 10-0946363 (registered on Mar. 2, 2010) titled "FRACTIONAL APPARATUS FOR SKIN-BEAUTY" capable of performing the above-described procedure includes a body provided with a radio frequency oscillator, a cable whose one end connects with the body, and a handpiece connecting with the other end of the cable and having a plurality of microneedles which is integrally installed at the end of the handpiece, electrically connects with the radio frequency oscillator of the body, is inserted into skin so as to deliver radio frequency, and moves in a line.

The microneedles are spaced apart from and coupled to a printed circuit board connected by the cable to the radio frequency oscillator, and some of the microneedles act as positive electrodes and the rest of the microneedles act as negative electrodes.

However, in the case of conventional microneedles, the plurality of microneedles are configured to have the same length despite the curved surface of skin to be treated. As a result, some of the microneedles are inserted into skin to deliver radio frequency while the rest are not rightly inserted into the skin, causing skin damage by means of heat.

As described above, conventional apparatuses used for improving skin have complex structures and problems of their own. Accordingly, there is a need to develop an apparatus for cleaning skin, which has a simple structure and operates reliably.

PRIOR ART DOCUMENT (Patent Document 1) South Korean Utility Model No. 20-0412689 (Mar. 23, 2006)
(Patent Document 2) South Korean Patent No. 10-1437563 (Aug. 28, 2014)

DETAILED DESCRIPTION OF THE INVENTION

Technical Problems

The present invention is directed to providing a handpiece of a skin care device which is capable of cleaning skin, improving skin etc. by injecting a solution into skin using a tip module contacting the skin and simultaneously absorbing ambient air, a substance such as waste products escaping from the skin etc. without using needles causing pain, a scar etc.

Further, the present invention is directed to providing a handpiece of a skin care device which allows a solution to be stably sprayed through a rotating tip module while rotating the tip module contacting skin in order to more effectively spray and inject the solution into the skin and further increase a skin improvement effect.

Technical Solutions

A handpiece of a skin care device according to an embodiment of the present invention includes a body part which includes an attaching and detaching hole provided on one side thereof, a solution introducing part linked with the attaching and detaching hole, and an air discharging part, and includes a disposable tip module mounted onto the attaching and detaching hole of the body part, wherein the tip module includes a cylinder body detachably mounted onto the attaching and detaching hole, and an inner cylinder configured to have a hollow inside and provided in the cylinder body, wherein the hollow inside of the inner cylinder is linked with the solution introducing part and is configured as a solution injection flow channel in which a solution introduced from the solution introducing part flows when the tip module is mounted onto the attaching and detaching hole, wherein the tip module includes an air suction flow channel configured to allow air between the cylinder body and the inner cylinder to flow and to discharge the air from the air discharging part according to the driving of an external suction pump, wherein the tip module includes a solution spraying part provided at the end of the inner cylinder so as to spray outwards a solution flowing in the solution injection flow channel such that ambient air and a substance escaping from skin, etc., are absorbed through the air suction flow channel according to the driving of the suction pump and are discharged from the air discharging part, while the end of the tip module contacts the skin, and sprays and injects the solution into the skin through the solution spraying part.

Further, the cylinder body preferably includes a first sealing member and a second sealing member installed around the circumference of the cylinder body, a groove part formed between the first sealing member and the second sealing member, and one or more linking holes formed at the groove part and linked with the hollow inside of the inner cylinder, wherein the cylinder body is sealed by the first sealing member and the second sealing member such that the solution introducing part is linked with the groove part when the tip module is mounted onto the attaching and detaching hole thereby allowing a solution introduced through the solution introducing part to be introduced into the solution injection flow channel of the hollow inside of the inner cylinder through the linking holes at the groove part.

Further, the cylinder body preferably includes an exposed part which is exposed to the outside of the attaching and detaching hole when the tip module is mounted onto the attaching and detaching hole, and a stepped part which is configured to be stepped inwards at the end of the exposed part, wherein the cylinder body is provided with an air suction flow channel which is formed between the end of the inner cylinder and the stepped part along the lengthwise direction, wherein the end of the exposed part contacts the skin, and air is sucked through the air suction flow channel according to the driving of the suction pump, such that negative pressure is formed at the stepped part, and that the skin is pulled by means of the negative pressure and comes into close contact with the end of the inner cylinder and the solution spraying part.

Further, the solution spraying part preferably includes a press-fitting member which is press-fitted into the end of the inner cylinder so as to block the solution injection flow channel, and is provided with one or more injection grooves along the lengthwise direction thereof such that a solution flowing in the solution injection flow channel is sprayed outwards through the injection grooves of the press-fitting member.

Further, the solution spraying part preferably includes a coupling cap which has one or more spraying holes and is coupled to the end of the inner cylinder so as to spray a solution flowing in the solution injection flow channel outwards through the spraying holes.

Further, the inner cylinder is preferably configured to have a closed end, and the solution spraying part includes one or more spraying holes formed at the closed end of the inner cylinder such that a solution flowing in the solution injection flow channel is sprayed outwards through the spraying holes.

Further, a handpiece of a skin care device preferably includes a driving motor which is provided to the other side of the body part and rotates a driving shaft, and a shaft coupling part which is coupled to the driving shaft and rotates together with the driving shaft and whose end is coupled to the tip module, wherein the tip module coupled to the shaft coupling part rotates while the shaft coupling part rotates by means of the driving shaft according to the driving of the driving motor, and a solution introduced through the solution introducing part is introduced into the solution injection flow channel through the linking holes at the groove part and is sprayed and injected into the skin through the solution spraying part while the tip module rotates in the state where the end of the tip module contacts skin.

Further, preferably, a handpiece of a skin care device further includes a friction surface which is formed at at least one of the end of the inner cylinder and the end of the solution spraying part so as to peel keratin by causing friction on the keratin of skin as the tip module rotates.

Advantageous Effects

A handpiece of a skin care device according to an embodiment of the present invention has the advantage of cleaning skin, improving skin etc. by injecting a solution into skin using a tip module contacting the skin and simultaneously absorbing ambient air, a substance such as waste products escaping from the skin etc. without using needles causing pain, a scar etc.

Further, a handpiece of a skin care device according to an embodiment of the present invention has the advantage of allowing a solution to be stably sprayed through a rotating tip module while rotating the tip module contacting skin in order to more effectively spray and inject the solution into the skin and further increase a skin improvement effect.

BEST MODE FOR CARRYING OUT THE INVENTION

As a means to achieve the purposes of the present, preferred embodiments of the present invention will be described in detail with reference to the attached drawings. In describing the embodiments, like reference numerals and symbols denote like elements, and additional description regarding this will be omitted. First, configurations and operations according to preferred embodiments of the present invention will be described with reference to FIGS. 1 and 2.

Figure 1:
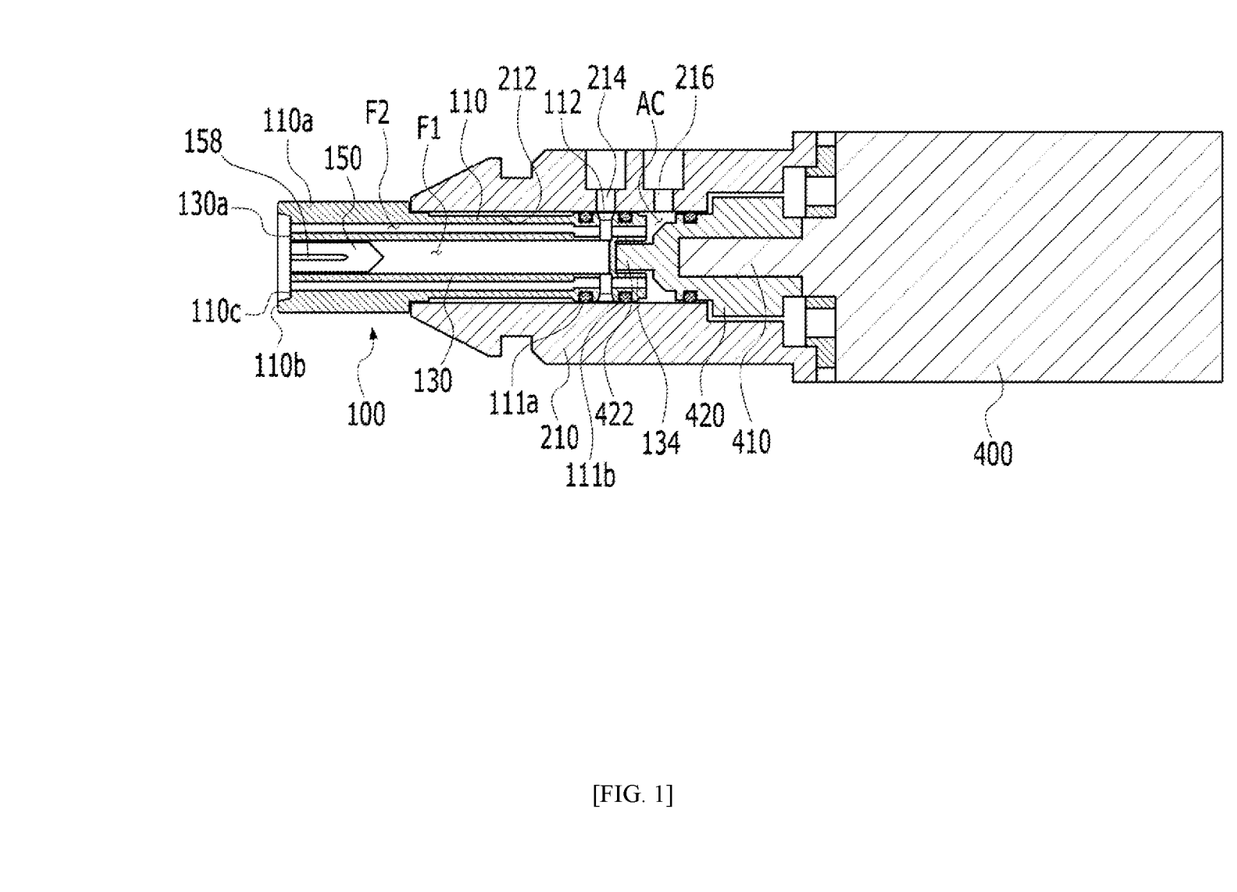
FIG. 1 is a side sectional view illustrating major elements of a handpiece of a skin care device according to an embodiment of the present invention.
Figure 2:
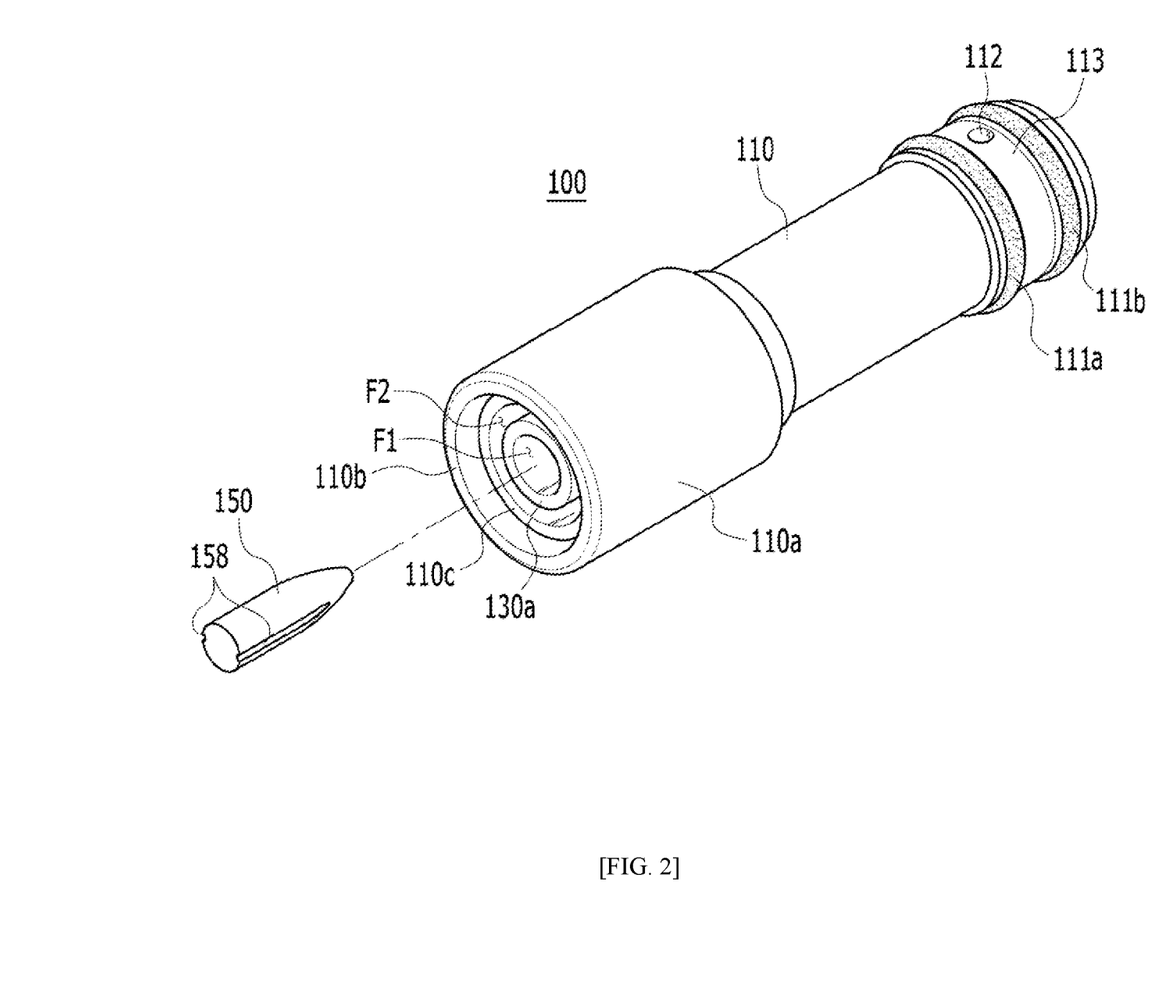
FIG. 2 is a view illustrating a configuration of an example of a tip module used for the handpiece in FIG. 1.

FIG. 1 is a side sectional view illustrating major elements of a handpiece of a skin care device according to an embodiment of the present invention and FIG. 2 is a view illustrating a configuration of an example of a tip module used for the handpiece in FIG. 1.

A handpiece of a skin care device according to an embodiment of the present invention, as illustrated in FIG. 1, basically includes a body part 210 installed inside an outer case (invisible) of the handpiece, and a tip module 100 detachably mounted on one side of the body part 210.

The body part 210 may be configured to include an attaching and detaching hole 212 and configured to form a solution introducing part 214 and an air discharging part 216 that are linked with the attaching and detaching hole 212, on one side thereof.

Additionally, the tip module 100 is detachably mounted onto the attaching and detaching hole 212 of the body part 210, operates by contacting the skin of a subject, and is configured to be disposable. That is, once a tip module is fitted into the attaching and detaching hole and used for a subject, the tip module is removed, and a new tip module is fitted into the attaching and detaching hole and used for another subject.

The tip module 100 may be configured to include a cylinder body 110 detachably mounted onto the attaching and detaching hole 212, and an inner cylinder 130 configured to have a hollow inside and installed in the cylinder body 110.

Preferably, the hollow inside of the inner cylinder 130 is configured to be linked with the solution introducing part 214 of the body part 210 when the tip module 100 is mounted onto the attaching and detaching hole 212, such that the hollow inside of the inner cylinder 103 is configured as a solution injection flow channel F1 where a solution introduced from the solution introducing part 214 flows.

Herein, the solution means a liquid or gaseous drug that is injected into skin through a follicle etc. of skin so as to remove waste products within follicles and to help improve skin and may also mean a drug mixed with compressed air.

Though not illustrated in the drawings, the solution introducing part 214 of the body part 210 is preferably configured to connect with an external solution supply source (invisible) by a tube or a pipe etc. such that a solution is supplied from the solution supply source the to the solution introducing part 214 through the tube or pipe and is introduced into the tip module.

Further, the air discharging part 216 of the body part 210 is preferably configured to connect with an external suction pump (invisible) such that air is sucked from the tip module 100 and pulled toward the suction pump through the air discharging part 216 depending on operations of the suction pump.

Meanwhile, the tip module preferably includes an air suction flow channel F2 such that a solution introduced into the solution introducing part 214 is introduced into the solution injection flow channel F1 while air flows between the cylinder body 110 and the inner cylinder 130 according to the drive of the external suction pump so as to be discharged through the air discharging part 216 when the tip module 100, as described above, is mounted onto the attaching and detaching hole 212.

Additionally, the tip module 100 is provided at the end of the inner cylinder 130 and includes a solution spaying part for spraying a solution flowing in the solution injection flow channel F1 outwards.

Herein, the solution spraying part may be realized in various examples, and FIGS. 1 and 2 illustrate a press-fitting member 150 as such an example.

FIG. 2 illustrates the press-fitting member 150 in more detail.

As illustrated in FIGS. 1 and 2, the press-fitting member 150, a solution spraying part, is press-fitted into the end of the inner cylinder 130 so as to block the solution injection flow channel F1 and provided with one or more injection grooves 158 along the lengthwise direction of the press-fitting member 150 such that a solution flowing through the solution injection flow channel F1 is sprayed outwards through the injection grooves 158 of the press-fitting member 150.

That is, small holes are formed between the press-fitting member 150 and the inner cylinder 130 such that a solution is sprayed outwards by the injection grooves 158.

Accordingly, ambient air, a substance such as waste products escaping from the skin, etc., are absorbed through the air suction flow channel F2 according to the drive of an external suction pump so as to be discharged through the air discharging part 216, while the end of the tip module 100 contacts skin, and sprays and injects a solution into skin through the injection grooves 158 of the press-fitting member 150.

As described above, while a solution is sprayed and injected through a follicle of skin etc., the solution is injected into the skin. Accordingly, a substance such as a waste product etc. is effectively sucked and discharged thereby making it possible to clean and improve skin.

Meanwhile, the cylinder body 110 of the tip module 100, as illustrated in FIGS. 1 and 2, is preferably configured to include a first sealing member 111a and a second sealing member 111b installed on the opposite side of a side, into which the press-fitting member 150 of the cylinder body 110 is fitted, around the circumference of the cylinder body, a groove part 113 formed between the first sealing member 111a and the second sealing member 111b, and one or more linking holes 112 formed at the groove part 113 and configured to be linked with the hollow inside of the inner cylinder 130.

Accordingly, as illustrated in FIGS. 1 and 2, when the tip module 100 is mounted onto the attaching and detaching hole 212 of the body part 210, the groove part 113 is sealed by the first sealing member 111a and the second sealing member 111b such that the solution introducing part 214 of the body part 210 is linked with the groove part 113. Accordingly, a solution introduced through the solution introducing part 214 is introduced into the solution injection flow channel F1 of the hollow inside of the inner cylinder 130 through the linking holes 112 while filling the groove part 113.

As described above, the groove part 113 is sealed by the first sealing member 111a and the second sealing member 111b so as to be linked only with the solution introducing part 214. Accordingly, a solution introduced through the solution introducing part 214 is also stably introduced into the solution injection flow channel F1 through the linking holes 112 at the groove part 113 by means of the "rotation of the tip module 100" that will be described hereafter.

Meanwhile, a driving motor 400 and parts connected to the driving motor have not been described during description of FIG. 1 but will be described with reference to FIGS. 3 and 4.

Figure 3:
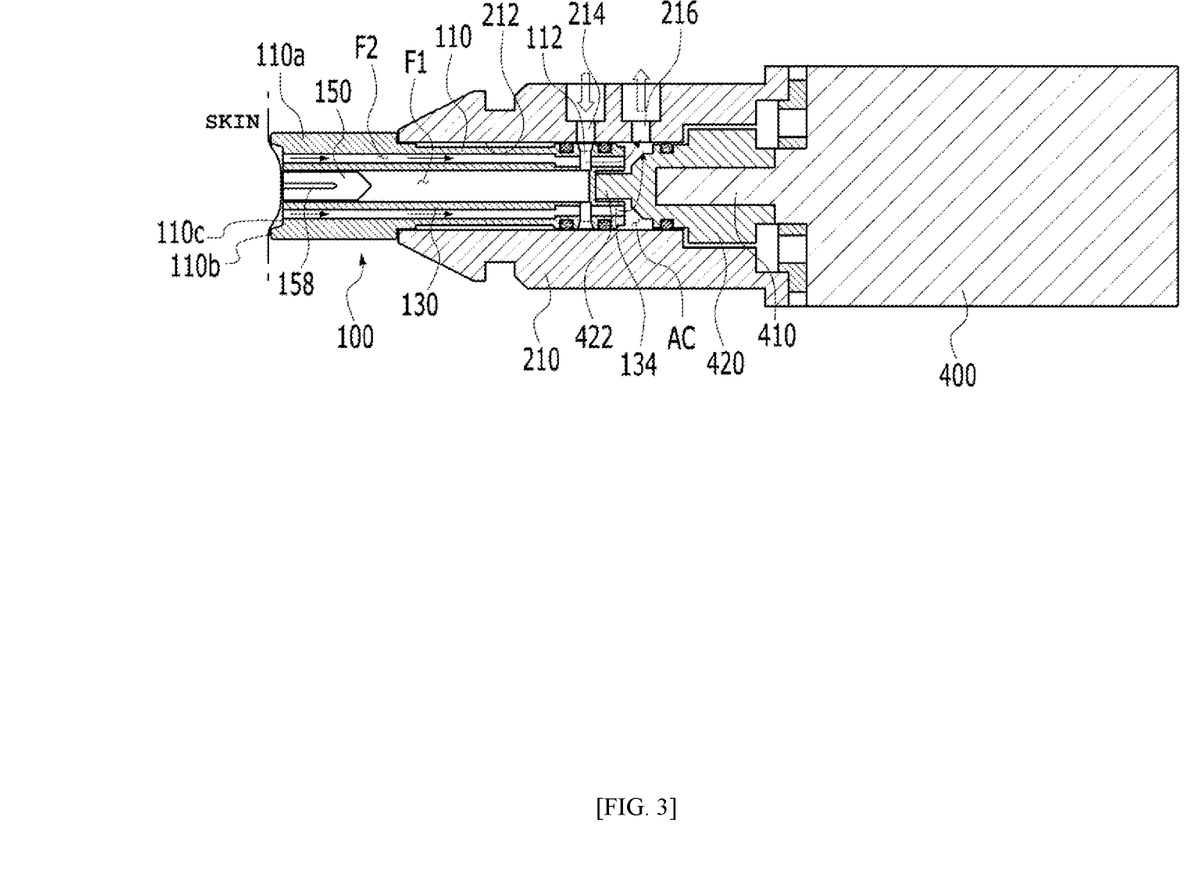
FIG. 3 is a view illustrating the operations, performed by the handpiece in FIG. 1, of sucking external air through an air suction flow channel by air suction and of pulling skin by means of negative pressure.
Figure 4:
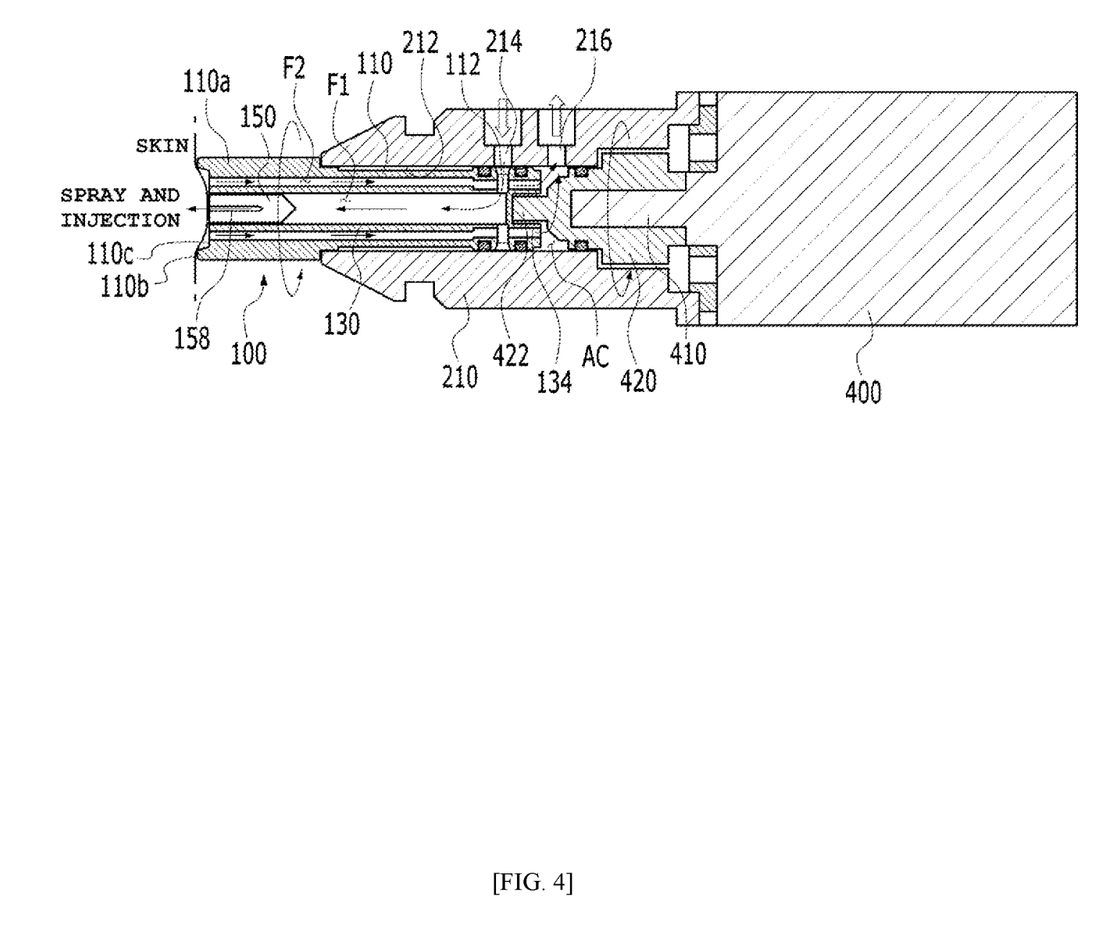
FIG. 4 is a view illustrating the operations, performed by the handpiece in FIG. 1, of introducing and spraying a solution when a tip module rotates according to operations of a driving motor.

FIGS. 3 and 4 illustrate operations of a handpiece of a skin care device with a configuration the same as that in FIG. 1, according to an embodiment of the present invention.

As illustrated in FIG. 3, when the tip module 100 is mounted onto the attaching and detaching hole 212, the cylinder body 110 of the tip module 100 preferably includes an exposed part 110a which has an external diameter larger than that of the attaching and detaching hole 212 so as to be exposed to the outside of the attaching and detaching hole 212, and a stepped part 110c which is configured to be stepped inwards at the end 110b of the exposed part.

The stepped part 110c, as described above, is formed at the end 110b of the exposed part, and the air suction flow channel F2, as illustrated in FIG. 3, is formed between the end of the inner cylinder 130 and the stepped part 110c along the lengthwise direction. Accordingly, the end 110b of the exposed part contacts skin, air is sucked through the air suction flow channel F2 according to the driving of an external suction pump (invisible), negative pressure is formed at the stepped part 110c, and the skin is pulled by means of the negative pressure so as to come into close contact with the end of the inner cylinder 130 and the end of the solution spraying part (press-fitting member 150).

As described above, air is sucked through the air suction flow channel F2, and skin is pulled by means of the negative pressure formed at the stepped part 110c such that solution sprayed and injected through the solution spraying part (press-fitting member 150) is better infiltrated into follicles of the skin.

Meanwhile, the above-described tip module 100 of a handpiece of a skin care device according to an embodiment of the present invention can spray a solution and suck air while rotating by means of a motor.

When the tip module 100 sprays a solution and sucks air while rotating, the solution can be evenly and effectively injected into skin.

FIG. 4 illustrates a rotating tip module 100 as described above.

A handpiece of a skin care device according to an embodiment of the present invention, as illustrated in FIG. 4, preferably includes a driving motor 400 provided to the rear of the attaching and detaching hole 212, onto which the tip module 100 of the body part 210 is mounted, so as to rotate a driving shaft 410, and a shaft coupling part 420 which is coupled to the driving shaft 410 so as to rotate together with the driving shaft 410 and whose end is coupled to the tip module 100.

As illustrated in FIG. 4, the tip module 100 coupled to the shaft coupling part 420 rotates while the shaft coupling part 420 rotates by means of the driving shaft 410 according to the driving of the driving motor 400, and in the state where the end of the tip module 100 contacts skin, the tip module 100 rotates, and a solution introduced through the solution introducing part 214 is introduced into the solution injection flow channel F1 through the linking holes 112 at the groove part 113 and is sprayed and injected into the skin through the solution spraying part (press-fitting member 150) while the skin is pulled towards the stepped part 110c by means of negative pressure through the air suction flow channel F2.

In this case, waste products of the skin etc. are sucked together with air and are introduced into an air compartment AC at the rear end of the tip module 100 through the air suction flow channel F2, and the air introduced into the air compartment AC is discharged outwards through the air discharging part 216 by an external suction pump.

As illustrated in FIG. 4, a tip coupling part 422 is formed at the end of the shaft coupling part 420, and coupling parts 134 coupled to the tip coupling part 422 are formed at the rear end of the tip module 100. Accordingly, the tip module 100 is inserted into the attaching and detaching hole 212, and the tip coupling part 422 are fitted into and coupled to the coupling parts 134 such that the tip module 100 is rotated by the driving shaft 410 and the shaft coupling part 420.

Figure 5:
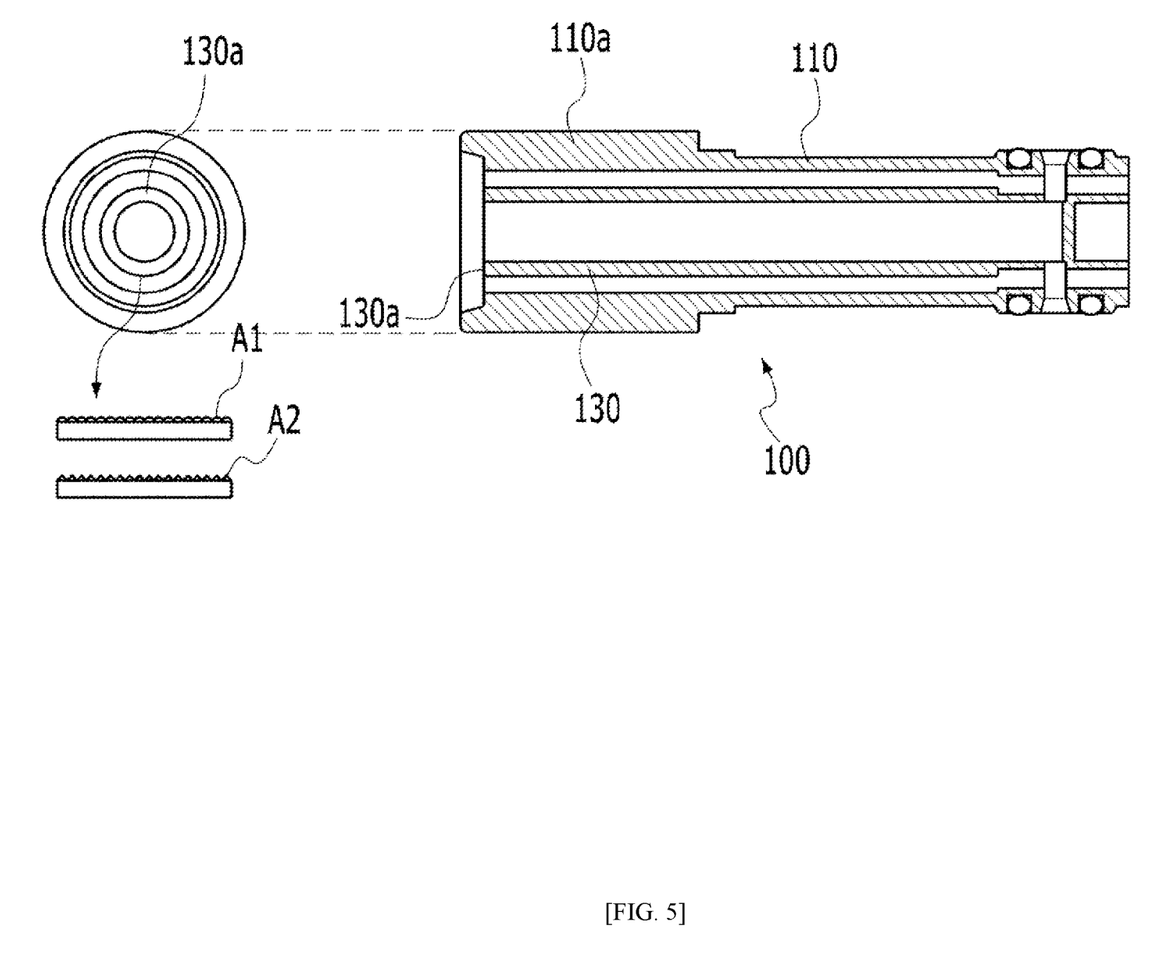
FIGS. 5 to 7 are views illustrating a handpiece of a skin care device according to another embodiment of the present invention.
Figure 6:
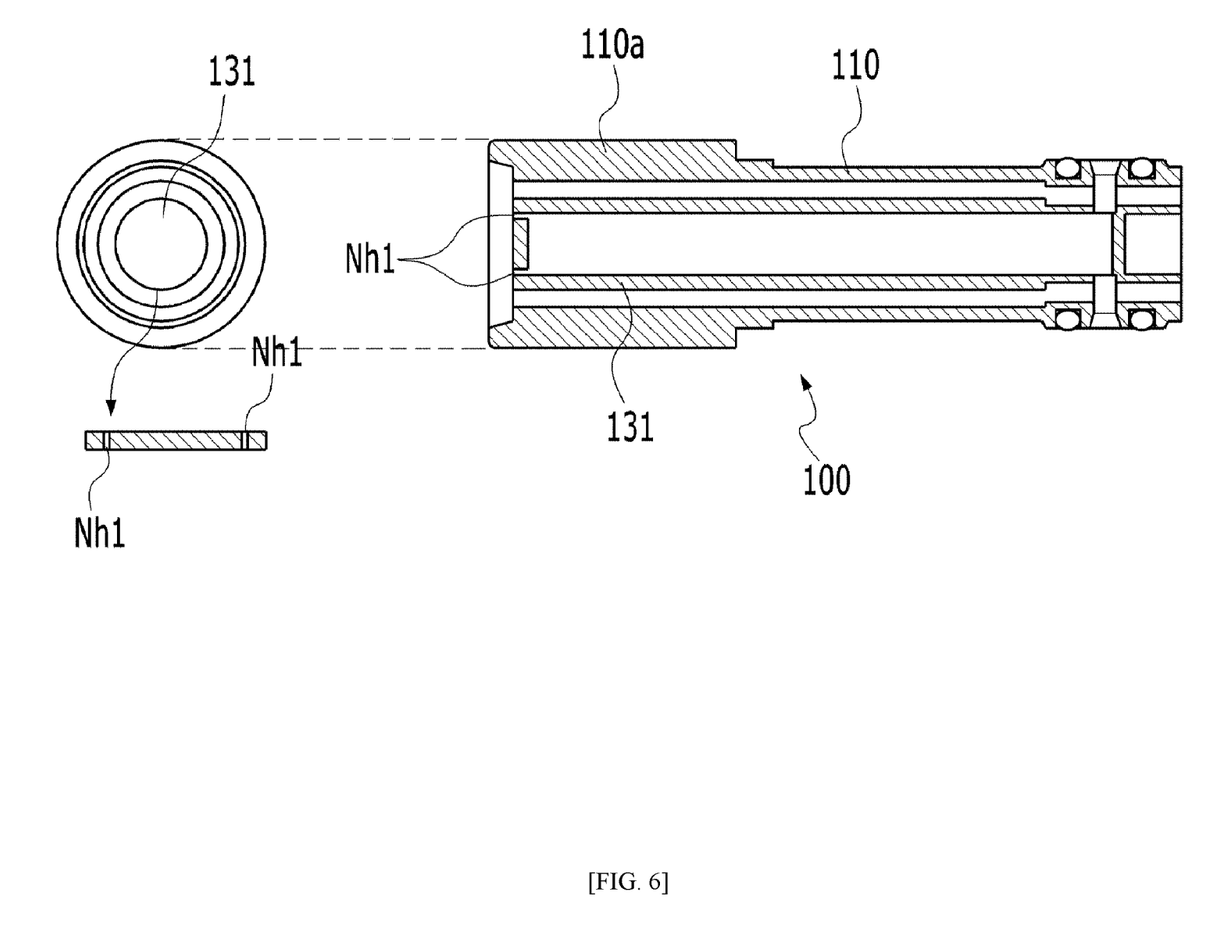
Figure 7:
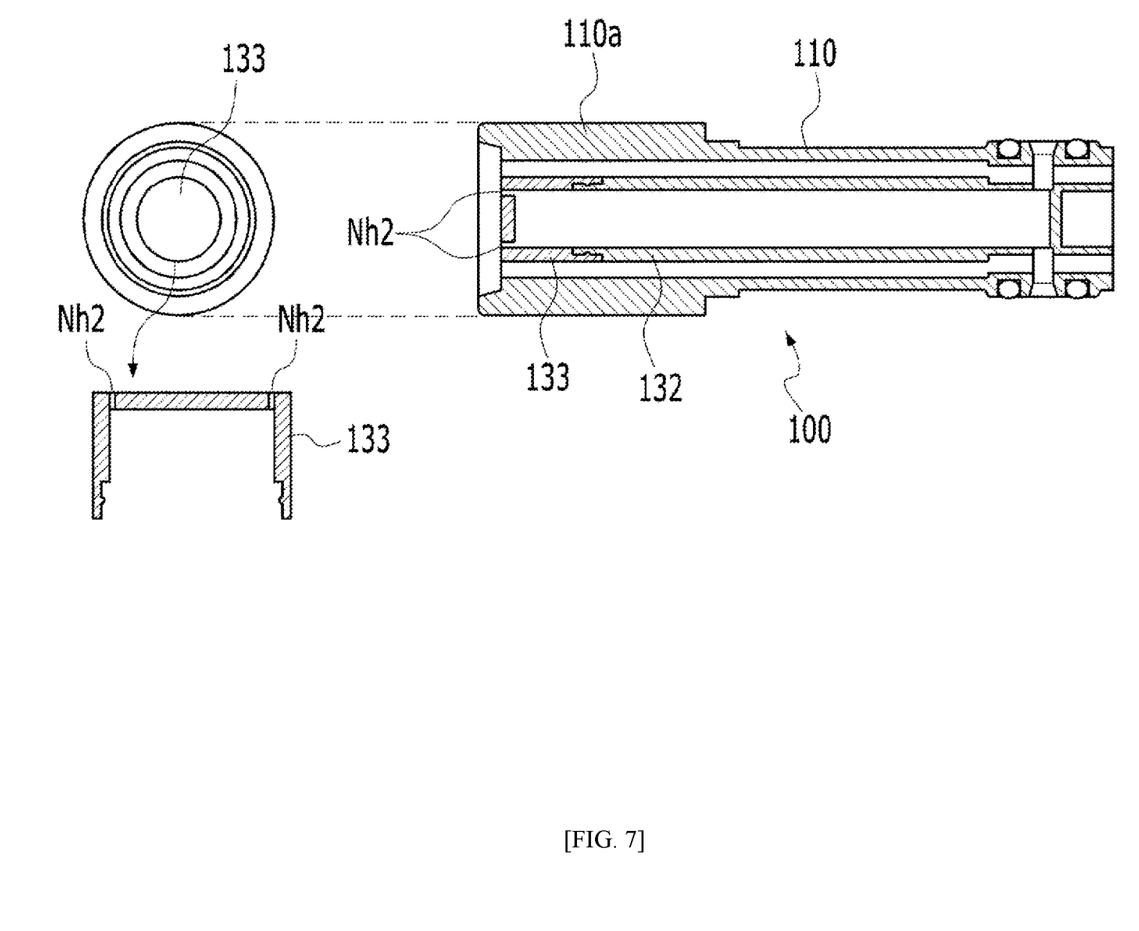

Meanwhile, a handpiece of a skin care device according to other embodiments of the present invention will be described with reference to FIGS. 5 to 7. A tip module applied to the present invention according to each embodiment illustrated in FIGS. 5 to 7 is different from the tip module according the embodiment that has been described above. The differences will be described, and parts that have already been described will be omitted.

According to the embodiment in FIG. 5, a tip module 100 at the end 130a of the inner cylinder 130 rotates as illustrated in FIG. 5 and forms a friction surface (A1 or A2) so as to peel keratin by causing friction on the keratin of skin.

The friction surface can be formed at the end 130a of the inner cylinder, can be formed at the solution spraying part (including not only the above-described press-fitting part 150 but also "a sealed end of the inner cylinder" that will be described hereunder and a "coupling cap"), and can be formed at both thereof. Because both parts contact skin, both parts form friction surfaces so as to peel keratin and at the same time spray a solution as describe above. Accordingly, a solution can be effectively injected.

As an example of the friction surface, an embossed part A1 or a serrated part A2, as illustrated in FIG. 5, can be formed.

Meanwhile, according to the embodiment in FIG. 6, a tip module 100 has an inner cylinder 131 whose end is closed, and a solution spraying part is configured as one or more spraying holes Nh1 formed at the closed end of the inner cylinder 131.

That is, instead of a press-fitting member, the end of the inner cylinder itself, as described above, is closed so as to be used as a solution spraying part, and small holes are made at the closed end so as to spray a solution.

According to this embodiment, a solution flowing in the solution injection flow channel F1 is sprayed outwards through the spraying holes Nh1.

Meanwhile, according to the embodiment in FIG. 7, a tip module 100 is configured as a result of coupling of an inner cylinder 132 and a coupling cap 133, and the coupling cap 133, as illustrated in FIG. 7, can be detachably coupled.

One or more spraying holes Nh2 are formed at the end of the coupling cap 133 and spray a solution flowing in a solution injection flow channel F1 outwards through the spraying holes Nh2.

A handpiece of a skin care device according to an embodiment of the present invention, as described above, is capable of spraying and injecting a solution through the pores of skin etc. and of effectively absorbing and discharging a substance such as waste products etc. escaping from the skin by means of the sprayed and injected solution without using needles, so as to clean and improve the skin.

Further, a handpiece of a skin care device of the present invention has the advantage of more effectively cleansing skin and of improving skin by allowing a solution to be sprayed and injected and by sucking air while the tip module rotates according to the driving of a driving motor, as described above.

INDUSTRIAL APPLICABILITY

A handpiece of a skin care device according to the present invention is applicable to the skin care industry in that it is capable of cleaning and improving skin by spraying and injecting a solution into skin using a tip module contacting the skin without inserting needles into the skin of a subject.

The invention claimed is:

1. A handpiece of a skin care device comprising:
a body part comprising an attaching and detaching hole provided on one side thereof, a solution introducing part linked with the attaching and detaching hole, and an air discharging part, and
a disposable tip module mounted onto the attaching and detaching hole of the body part,
wherein the tip module comprises a cylinder body detachably mounted onto the attaching and detaching hole, and an inner cylinder configured to have a hollow inside and installed in the cylinder body,
the hollow inside of the inner cylinder is linked with the solution introducing part and is configured as a solution injection flow channel in which a solution introduced from the solution introducing part flows when the tip module is mounted onto the attaching and detaching hole,
the tip module comprises an air suction flow channel configured to allow air between the cylinder body and the inner cylinder to flow and to discharge the air from the air discharging part according to a driving of an external suction pump, and the tip module comprises a solution spraying part provided at an end of the inner cylinder so as to spray outwards a solution flowing in the solution injection flow channel such that ambient air and a substance escaping from skin are absorbed through the air suction flow channel according to the driving of the suction pump and are discharged from the air discharging part, while an end of the tip module contacts the skin, and sprays and injects the solution into the skin through the solution spraying part, wherein the cylinder body comprises a first sealing member and a second sealing member installed around the circumference of the cylinder body, a groove part formed between the first sealing member and the second sealing member, and one or more linking holes formed at the groove part and linked with the hollow inside of the inner cylinder, and the cylinder body is sealed by the first sealing member and the second sealing member such that the solution introducing part is linked with the groove part when the tip module is mounted onto the attaching and detaching hole thereby allowing a solution introduced through the solution introducing part to be introduced into the solution injection flow channel of the hollow inside of the inner cylinder through the linking holes at the groove part.

2. The handpiece of a skin care device according to claim 1, wherein the solution spraying part comprises a press-fitting member which is press-fitted into the end of the inner cylinder so as to block the solution injection flow channel, and is provided with one or more injection grooves along the lengthwise direction thereof such that a solution flowing in the solution injection flow channel is sprayed outwards through the injection grooves of the press-fitting member.

3. The handpiece of a skin care device according to claim 1, wherein the inner cylinder is configured to have a closed end, and the solution spraying part comprises one or more spraying holes formed at the closed end of the inner cylinder such that a solution flowing in the solution injection flow channel is sprayed outwards through the spraying holes.

4. The handpiece of a skin care device according to claim 1, wherein the handpiece of a skin care device comprises a driving motor which is provided to an other side of the body part and rotates a driving shaft, and a shaft coupling part which is coupled to the driving shaft and rotates together with the driving shaft and whose end is coupled to the tip module, the tip module coupled to the shaft coupling part rotates while the shaft coupling part rotates by means of the driving shaft according to the driving of the driving motor, and a solution introduced through the solution introducing part is introduced into the solution injection flow channel through the linking holes at the groove part and is sprayed and injected into the skin through the solution spraying part while the tip module rotates in a state where the end of the tip module contacts skin.

5. The handpiece of a skin care device according to claim 4, wherein the handpiece of a skin care device further comprises a friction surface which is formed at at least one of an end of the inner cylinder and the end of the solution spraying part so as to peel keratin by causing friction on a keratin of skin as the tip module rotates.

* * * * *